(12) United States Patent
Kitagawa et al.

(10) Patent No.: US 9,428,728 B2
(45) Date of Patent: Aug. 30, 2016

(54) CARRIER FOR UNDIFFERENTIATED CELL CULTURE AND SUBCULTURE METHOD THEREOF

(75) Inventors: Fumihiko Kitagawa, Kanagawa (JP); Takafumi Imaizumi, Kanagawa (JP); Katsunori Sasaki, Nagano (JP)

(73) Assignee: COORSTEK KK, Tokyo (JP)

( * ) Notice: Subject to any disclaimer, the term of this patent is extended or adjusted under 35 U.S.C. 154(b) by 853 days.

(21) Appl. No.: 11/984,544

(22) Filed: Nov. 19, 2007

(65) Prior Publication Data
US 2008/0118976 A1   May 22, 2008

(30) Foreign Application Priority Data

| Nov. 21, 2006 | (JP) | 2006-313835 |
| Mar. 12, 2007 | (JP) | 2007-062059 |
| Jun. 15, 2007 | (JP) | 2007-158237 |

(51) Int. Cl.
*C12N 5/00* (2006.01)
*C12N 5/0735* (2010.01)

(52) U.S. Cl.
CPC ........... *C12N 5/0068* (2013.01); *C12N 5/0606* (2013.01); *C12N 2533/14* (2013.01)

(58) Field of Classification Search
None
See application file for complete search history.

(56) References Cited

U.S. PATENT DOCUMENTS

| 5,449,620 | A | 9/1995 | Khillan | |
| 5,512,474 | A * | 4/1996 | Clapper et al. | 435/402 |
| 5,731,417 | A | 3/1998 | Swiderek et al. | |
| 6,340,648 | B1 | 1/2002 | Imura et al. | |
| 6,667,159 | B1 * | 12/2003 | Walt et al. | 435/7.32 |
| 6,900,055 | B1 | 5/2005 | Fuller et al. | |
| 7,723,395 | B2 | 5/2010 | Ringeisen et al. | |
| 8,262,957 | B2 | 9/2012 | Fukushima et al. | |
| 2005/0106725 | A1 | 5/2005 | Palecek et al. | |
| 2005/0170089 | A1 | 8/2005 | Lashmore et al. | |
| 2005/0230272 | A1 * | 10/2005 | Lee et al. | 205/792 |
| 2005/0246021 | A1 | 11/2005 | Ringeisen et al. | |
| 2010/0099547 | A1 | 4/2010 | Fukushima et al. | |

FOREIGN PATENT DOCUMENTS

| JP | 59-143586 A | 8/1984 |
| JP | 06-007148 A | 1/1994 |
| JP | 2000-157623 A | 6/2000 |
| JP | 2000-302567 A | 10/2000 |
| JP | 2002-017846 A | 1/2002 |
| JP | 2002-528567 A | 9/2002 |
| JP | 2002-335949 A | 11/2002 |
| JP | 2003-116519 A | 4/2003 |
| JP | 2005-027598 A | 2/2005 |
| JP | 2005-253412 A | 9/2005 |
| JP | 2006-296253 A | 11/2006 |
| JP | 2006-304734 A | 11/2006 |
| JP | 2007-167063 A | 7/2007 |
| JP | 2007-202506 A | 8/2007 |
| JP | 2007-209203 A | 8/2007 |
| JP | 2008-148685 A | 7/2008 |
| JP | 2008-195595 A | 8/2008 |
| WO | WO 01/36013 A1 | 5/2001 |
| WO | WO 03/038070 A1 | 5/2003 |
| WO | WO 2004/048064 A1 | 6/2004 |

OTHER PUBLICATIONS

JPA—2005-027598—English translation of JP 2005-027598 on Applicant IDS.*
Josset et al., In vitro reactions of human osteoblasts in culture with zirconia and alumina ceramics, J. Biomed. Mater. Res., 47, pp. 481-493, 1999.*
Piconi et al., Zirconia as a ceramic biomaterial, Biomaterials 20, pp. 1-25, 1999.*
Inoue et al., On-Chip culture system fo observation of isolated individual cells, Lab on a Chip, 2001, 1, 50-55.*
A. Almirall et al., "Fabrication of low temperature macroporous hydroxyapatite scaffolds by foaming and hydrolysis of an a-TCP paste", Biomaterials, Elsevier Science Publishers B.V., vol. 25, No. 17, Aug. 2004, pp. 3671-3680.
J. Zhang et al., "A comparative study of porous scaffolds with cubic and spherical macropores", Polymer, Elsevier Science Publishers B.V., vol. 46, No. 13, Jun. 17, 2005, pp. 4979-4985.
V. Karageorgiou et al., "Porosity of 3D biomaterial scaffolds and osteogenesis", Biomaterials, Elsevier Science Publishers B.V., vol. 26, No. 27, Sep. 2005, pp. 5474-5491.
Y. Sakka et al., "Fabrication of porous ceramics with controlled pore size by colloidal processing", Science and Technology of Advanced Materials, Elsevier, vol. 6, No. 8, Nov. 2005, pp. 915-920.
C. San Marchi et al., "Deformation of Open-Cell Aluminum Foam", Acta Materialia Inc., Nov. 14, 2001, No. 49, pp. 3959-3969.
SPI Supplies "ANOPORETM Inorganic Aluminum Oxide Membrane Filters" SPI Supplies Catalog, [online], Structure Probe, Inc., Jan. 17, 2003 [retrieved on May 22, 2009]. Retrieved from the Internet: <URL: http://web.archiva.org/web/20030117185743/ http://www.2spi.com/catalog/spec_prep/filter2.shtml>, 3 pages.
F. Kitagawa, U.S. PTO Official Action, U.S. Appl. No. 11/561,055, dated Mar. 19, 2014, 26 pages.
Mann, M; Shter, G.E.; Grader, G.S., "Effect of Sintering on Ti02-Impregnated Alumina Foams" J. Mat. Sci, 2002, 37,4049-4055.
Li, Shu-Tung; Chen, Hui-Chen; Pierson, Darlene; Yuen, Debbie; and Hansen, Peggy "NuOss®, a Bone Grafting Material for Oral Surgery: Comparative Study with BioOss®", Stoma Science, Jul. 15, 2000, 3 pages.
Sepulveda, P; Bressiani, A.H; Bressiani, J.C; Meseguer, L; Konig Jr, B, "In Vivo Evaluation of Hydroxyapatite Foams" Mater. Res., 2002, 5(3), 253-256.

(Continued)

*Primary Examiner* — Taeyoon Kim
*Assistant Examiner* — Srikanth Patury
(74) *Attorney, Agent, or Firm* — Foley & Lardner LLP

(57) ABSTRACT

A colony (cell mass) proliferated under the undifferentiated state is obtained by using a carrier for cell culture in which two or more of a concavity having a porous body in a surface are arranged on a substrate surface in the form of a matrix, inoculating an undifferentiated cell on at least one concavity of the carrier for culture and carrying out culture.

10 Claims, 10 Drawing Sheets

(56) References Cited

OTHER PUBLICATIONS

Xinshuang Guo; Zhufa Zhou; Shumei Wang; Song Zhao; Qiang Zhang; Guilin Ma, "A novel method for preparation of interconnected pore-gradient ceramic foams by gelcasting" J.Porous Mater., Oct. 2012 (pub. on line Dec. 4, 2011 ), 19(5), pp. 853-858.
Nakata, M et al. "Fabrication Alumina Sintered Bodies by Gelate-Freezing Method" J Ceram Soc Japan, 2005, 113(11), pp. 712-715.
Banhart, John "Manufacture, Characterisation and Application of Cellular Metals and Metal Foams" Progress in Materials Science, 2001,46,pp. 559-632.
Tech-On, Jun. 22, 2007, URL http://techno.nikkeibp.co.jp/article/NEWS/20070622/134654/.
Covalent Materials Corporation, Press Release, Jun. 19, 2007, URL http://www.covalent.co.jp/jpn/corporate/release/n20070619.html.
F. Kitagawa, U.S. PTO Official Action, U.S. Appl. No. 11/561,055, dated Nov. 5, 2014.
Coil, "Corrosion Resistance of Continuously Anodised Aluminium", Product Characterization. Part 1 (1.6), Nov. 2005, pp. 1-10.
Proceedings of the Japanese Society for Biomaterials Convention, Nov. 28, 2005, vol. 27, p. 301.
M. Dalby et al., "Osteoprogenitor response to defined topographics with nanoscale depths", Biomaterials, Mar. 2006, vol. 27, No. 8, pp. 1306-1315.
F. Kitagawa, U.S. PTO Notice of Allowance, U.S. Appl. No. 11/561,055, dated Apr. 7, 2015, 10 pages.

\* cited by examiner

CARRIER FOR UNDIFFERENTIATED CELL CULTURE AND SUBCULTURE METHOD THEREOF

This application claims priority from Japanese Patent Application No. 2006-313835 filed Nov. 21, 2006, Japanese Patent Application 2007-062059 filed Mar. 12, 2007, and Japanese Patent Application 2007-158237 filed Jun. 15, 2007, which are incorporated herein by reference in their entirety.

BACKGROUND OF THE INVENTION

1. Field of the Invention

The present invention relates to techniques for culturing undifferentiated cells having pluripotency such as an embryonic stem cell (ES cell), and a multipotential adult stem cell, particularly a carrier for culture suitable for subculture and the like and a method for culturing a cell using the same.

2. Brief Description of the Background Art

In recent years, accompanied by the advance in the development on the separation of a stem cell from human bone marrow fluid, its differentiation induction into an object tissue cell, its three dimensional culture techniques, its scaffold material and the like, it became possible to produce tissues such as the skin, a bone, a cartilage, a blood vessel, a cardiac valve and a ligament from the stem cell by cell culture, and clinical application has already been started on a part thereof.

On the other hand, since undifferentiated cells typified by the ES cell are cells having such a totipotency by which the cells can be differentiated into all of other tissue cells, the cells are expected to be applied to the regeneration medical treatment.

Thus, studies have been energetically carried out on the method for inducing differentiation of undifferentiated cells into tissue cells. In order to use the ES cell for the purpose of regeneration medical treatment, a technique is necessary for mass-proliferating an ES cell line which is produced by fusing a nucleus-removed ovum with somatic cell nucleus of other individual.

Up to now, it has been confirmed that mouse ES cell can keep its undifferentiation property when co-cultured on a feeder cell typified by STO (mouse fetal fibroblast) and the like in the presence of LIF (leukemia inhibitory factor) (e.g., see Non-patent Reference 1).

Additionally, some reports have been published recently on the establishment of human ES cell strains also from human blastocysts, which have pluripotency and can perform cell division in the undifferentiated state for a long time.

As the general carriers for culture for proliferating or maintaining undifferentiated cells typified by ES cell and the like as described above, a plastic dish coated by biogenic compound such as collagen, gelatin, laminin and matrigel, wherein a mouse-derived or human tissue-derived feeder cell is proliferated, are conventionally used.

On the other hand, as a carrier for culture suited for the mass culture of a spherical cell mass, Patent Reference 1 discloses a cell culture tip equipped with a cell culture cell which keeps feeder cells regularly arranged in an array or honeycomb shape, by aggregating them, on the surface of a substrate consisting of inorganic material such as glass, metallic material such as stainless steel, synthetic resin, rubber or the like.

[Patent Reference 1] JP-A-2005-27598

[Non-patent Reference 1] Li Cui, Katsunori Sasaki, *The Journal of Histochemistry and Cytochemistry,* 2004, 52, p. 1447-1457

SUMMARY OF THE INVENTION

However, when ES cell is proliferated on the aforementioned carrier for culture, since the cell forms a flat colony (cell mass), and the undifferentiated state possessed by the ES cell disappears as it becomes gigantic.

Thus, for example, for the purpose of sub-culturing mouse ES cell, the following method is used. Namely, the ES cell is proliferated and maintained by observing the ES cell colony under a microscope, and exfoliating the colony from its carrier for culture by trypsin treatment to separate a single cell when it becomes a certain degree of size, followed by carrying out subculture on another carrier.

According to the method, since it is difficult to control size of the obtained ES cell colony, size of the obtained ES cell colony does not become constant. Thus, it is difficult to judge the timing of carrying out the subculture. There is a problem that a differentiated cell and an undifferentiated cell are present as a mixture when the timing is misjudged.

Additionally, in a case of the ES cell of primates such as human and monkey, when trypsin treatment is carried out in order to exfoliate the colonized culture cell from the carrier for culture and thereby to obtain a single cell, the cell cannot survive, which is different from the case of mouse ES cell.

Accordingly, for example, maintenance of cells of the primates is carried out by a method in which an ES cell colony is fractionized in parts by carrying out enzyme treatment with collagenase and trypsin and subsequent pipetting and then re-inoculated onto other carrier.

The cell mass cultured from the ES cell colony collected in the manner has a problem that its size is irregular and the differentiation induction using it is also apt to become irregular.

The present invention has been made for dissolving the aforementioned technical problems. The purpose of the present invention is to provide a carrier for cell culture which can efficiently proliferate an undifferentiated cell such as a human ES cell into a uniform size and also can culture the cell with keeping its undifferentiated state, and a method for culturing the cell.

BRIEF DESCRIPTION OF THE DRAWINGS

FIG. 1 is an electron microphotograph (20,000 magnifications) of the alumina ceramics porous body which constitutes the carrier for culture in Example 1.

FIG. 2 is a microphotograph (50 magnifications) of cultured cells on the carrier for culture in Example 1 after alkaline phosphatase staining.

FIG. 3 is a microphotograph (50 magnifications) of the carrier for culture in Example 1 after pipetting.

FIG. 4 is an electron microphotograph (20,000 magnifications) of the alumina ceramics compact body which constitutes the carrier for culture in Comparative Example 1.

FIG. 5 is a microphotograph (50 magnifications) of cultured cells on the carrier for culture in Comparative Example 1 after alkaline phosphatase staining.

FIG. 6 is a microphotograph (50 magnifications) of the carrier for culture in Comparative Example 1 after pipetting.

FIG. 7 is an electron microphotograph (100 magnifications) of the carrier for culture in Comparative Example 2.

DETAILED DESCRIPTION OF THE INVENTION

Figure 1:
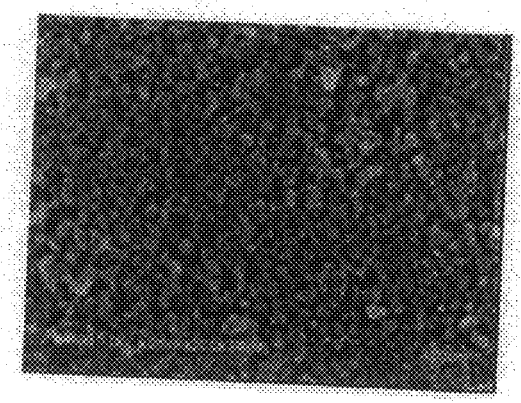

A carrier for cell culture of the present invention is a carrier for cell culture in which two or more of a concavity having a porous body in a surface are arranged on a substrate surface in the form of a matrix.

When the aforementioned carrier for cell culture is used, control of size of a colony of an differentiated cell such as ES cell is possible, and exfoliation (recovery) of the cultured cell from the carrier for culture also becomes easy. Therefore, efficient culturing with superior operability can be carried out.

According to the carrier for cell culture, it is preferable that the substrate surface consists of a porous body.

When the whole carrier for cell culture is a porous body, adhesion of the cultured cell to the carrier for cell culture and its exfoliation therefrom can be carried out efficiently.

Also, it is preferable that the concavity has a diameter of from 10 μm to 1,000 μm and a depth of from 30 μm to 1,000 μm; and the aforementioned porous body has a pore size of 10 nm to 2,000 nm.

In general, since the ES cell colony loses its undifferentiated state when it becomes a certain size or more, it is preferable that the concavity size is within the range described above, and when pore size of the porous body is within the range described above, the cultured cell can be easily adhered to the inside of the concavity and can be easily peeled off by pipetting.

Also, in view of the easy production of the carrier for culture, easy operation of the cultured cell and the like, it is preferable that bottom face of the concavity has a hemispheric shape.

Such a shape of concavity is preferable in view of the formation of a spherical cell mass, exfoliation ability thereof and the like, particularly when the cell mass exfoliated from the aforementioned carrier for culture is used in suspension culturing.

Particularly, it is preferable that the concavity of the carrier for culture has a diameter of from 100 μm to 400 μm and a depth of from 50 μm to 400 μm when it is used in culture of a mouse ES cell, while it is preferable that the concavity of the carrier for culture has a diameter of from 250 μm to 1,000 μm and a depth of from 125 μm to 1,000 μm when it is used in culture of a human ES cell.

Additionally, it is preferable that the substrate consists of at least one of ceramics among zirconia, yttria, titania, alumina, silica, hydroxyapatite and β-calcium tertiary phosphate or of glass.

These ceramics or glass are suitably used, since they do not accelerate differentiation induction of undifferentiated cells and therefore have high biogenic stability.

The method of the present invention for culturing a cell comprises by using the carrier for culture, inoculating an undifferentiated cell on at least one concavity of the carrier for culture and carrying out culture to obtain a cell mass proliferated under the undifferentiated state.

By culturing an undifferentiated cell using the carrier for culture in the present invention, the undifferentiated cell can be efficiently cultured in a large amount without causing differentiation.

Additionally, the method of the present invention for culturing a cell comprises carrying out a subculture by repeating the method for culturing described above, by separating the cell mass obtained by the culture described above into a single cell or a small cell population, and using the undifferentiated cell obtained by exfoliation from the carrier for culture described above.

When the carrier for culture in the present invention is used, since the same culturing operation can be repeatedly carried out easily, efficient subculture can be carried out.

According to the subculture method, separation of cell mass can be easily carried out by enzyme treatment and pipetting.

By using the carrier for culture in the present invention from which the cultured cell can be easily exfoliated, the peeling and separation operation of cultured cell from the carrier for culture can be easily carried out and its efficiency can be improved.

Additionally, another embodiment of the method in the present invention for culturing a cell comprises carrying out suspension culture by exfoliating the cell mass obtained in the above from the carrier for culture in the state of cell mass, and using the cell mass of undifferentiated cell.

In the manner, the cell mass of undifferentiated cell can be suitably applied to not only its subculture but also suspension culture, and embryoid body (EB) can be easily obtained from ES cell by the suspension culture.

Exfoliation of cell mass from the carrier for cell culture can be carried out by pipetting alone.

By the use of the carrier for culture of the present invention, exfoliation from the carrier for culture becomes easy without carrying out the trypsin treatment. Two or more uniform call masses can be obtained without damage by the enzyme treatment.

The undifferentiated cell obtained by culturing it by the method described above can be cultured with keeping expression of an undifferentiation marker.

The following describes the present invention further in detail.

In the carrier for cell culture of undifferentiated cell use of the present invention, two or more of a concavity having a porous body in a surface are arranged on a substrate surface in the form of a matrix.

In this connection, the term "in the form of a matrix" as used herein means that they are arranged in the line direction and column direction, and it is preferable that the line direction and column direction intersect one another almost orthogonally.

By the use of such a shape of carrier for culture, it becomes possible to effect cell proliferation only on inside of the concavity formed on the substrate surface, and control of the size of colony of undifferentiated cell such as ES cell can be carried out.

That is, since the ES cell or the like have a property to slowdown its proliferation when it is cultured and reaches the size of the concavity, a predetermined size of cell mass can be obtained without observing all the time. By using a concavity having such a size which can maintain undifferentiation, proliferation of an undifferentiated cell having a controlled size becomes easy.

Also, when the surface of the aforementioned concavity is constructed by a porous body, the cultured cell is easily adhered to the inside of the concavity of carrier for culture and exfoliation therefrom also becomes easy. Thus, when the cultured cell is recovered, it becomes possible to exfoliate the cultured cell easily by pipetting alone, without requiring the enzyme treatment for a long time which is particularly undesirable in the case of human ES cell and the like.

Additionally, from the viewpoint of reducing adhering area of the cultured cell to the carrier for culture, it is further preferable that not only the concavity but also the whole carrier for culture including the substrate surface consists of the porous body.

By this, adhesion of the cultured cell to said carrier for culture and exfoliation therefrom can be carried out further efficiently.

In this connection, it is preferable that the concavities are regularly arranged.

When the aforementioned concavities are regularly arranged in this way, it becomes possible to carry out the pipetting mechanically and cell masses having uniform size can be obtained. Therefore, efficient and uniform mass production of the cultured cell becomes possible.

It is preferable that the concavity has a diameter of from 10 μm to 1,000 μm and a depth of from 30 μm to 1,000 μm.

In general, since the ES cell colony loses its undifferentiated state when it becomes a certain size or more, it is preferable from the viewpoint of keeping the undifferentiated state that the concavity size is within the range described above.

Also, it is preferable that the porous body has a pore size of from 10 nm to 2,000 nm.

When such a porous body is used, the cultured cell can be easily adhered to the inside of the concavity and can be easily exfoliated by pipetting.

Shape of the concavity is not particularly limited and various shapes can be used, as long as it can be processed on the substrate surface with the size described above.

Particularly, when the cell mass exfoliated from the carrier for cell culture of the present invention is used in its suspension culturing, it is preferable in vie of the exfoliation ability, shape of the formed colony and the like that the bottom face has a hemispheric shape.

In this connection, the size of concavity is expressed by diameter and depth in the present invention. When the opening face has a polygonal shape, the "diameter of concavity" according to the present invention is a diameter of a case in which the opening area of concavity on the substrate surface of the carrier for culture is replaced by a circle. Also, the depth is a depth of the deeper part of the concavity.

Additionally, it is preferable that the aforementioned size of concavity is a diameter of from 1 time to 100 times, based on the size of the cell to be cultured.

In the case of a cell mass proliferated in a concavity having the aforementioned size, since a uniform size can be obtained and its recovery by pipetting and the like can be made easily, efficient culturing can be carried out.

In this connection, although the concavity having the same size of a cell can maintain the undifferentiated state of the cell, there is not so much room for its proliferation. Since it is preferable that the cell does not jut out from the concavity, a diameter of 2 times or more is more preferable.

Additionally, 25 times or less is further preferable for the purpose of improving accuracy of undifferentiation.

Size of one ES cell is about 10 μm in diameter. In order to prevent proliferation of the cell on the outside of the concavity, preferable diameter of the concavity is, 10 μm or more and its preferable depth is 30 μm or more.

On the other hand, when the size of concavity is too large, there is a danger of causing differentiation of the cell since cell mass of the proliferated undifferentiated cell becomes too large. Therefore, it is preferable that diameter of the concavity is 1,000 μm or less and its depth is 1,000 μm or less.

Particularly, when the carrier for culture is used in culture of mouse ES cell, it is preferable that the concavity has a diameter of from 100 μm to 400 μm and a depth of from 50 μm to 400 μm.

When the concavity has a diameter of less than 100 μm and a depth of less than 50 μm, the concavity is so small as the proliferating space of mouse ES cell that it causes inconveniences in the pipetting operation and the like at the time of medium exchange, such as the aptness to suck the cultured cell.

More preferably, the concavity has a diameter of 200 μm or more and a depth of 100 μm or more.

On the other hand, when the concavity has a diameter of exceeding 400 μm and a depth of exceeding 400 μm, the concavity is so large as the proliferating space of mouse ES cell that a preferable ES cell colony cannot be formed.

Also, when the aforementioned carrier for culture is used in the culturing of human ES cell, it is preferable that the concavity has a diameter of from 250 μm to 1,000 μm and a depth of from 125 μm to 1,000 μm.

In the case of the ES cell of primates such as human and monkey, when its trypsin treatment is carried out to obtain a single cell, the cell cannot survive as described above. Thus, since it is necessary to allow two or more cells to form a cell mass in which they are linked with one another, it is preferable that the size of concavity is within the range described above which is larger than the mouse ES cell.

As the substrate of the carrier for culture of the present invention, non-metal inorganic materials are preferable. Particularly, ceramics or glass is suitably used. The illustrative materials include zirconia, yttria, titania, alumina, silica, alumina-silica, hydroxyapatite, β-calcium tertiary phosphate and the like, which have high safety for the living body. Among them, alumina, zirconia, hydroxyapatite, β-calcium tertiary phosphate and titania in which their safety for the living body has been confirmed are more preferable. Particularly, zirconia or hydroxyapatite is preferable.

Additionally, the method of the present invention for culturing a cell comprises by using the carrier for culture of the present invention, inoculating an undifferentiated cell on at least one concavity of the carrier for culture and carrying out culture to obtain a cell mass proliferated under the undifferentiated state.

By using the aforementioned carrier for culture having a specific shape, an undifferentiated cell can be efficiently cultured into a uniform size and in a large amount without causing differentiation, and the resulting cell mass can be easily exfoliated from the carrier for culture.

In the conventional methods for culturing cells, for example, a feeder cell layer by a mitomycin-treated MEF (mouse embryonic fibroblast) or the like is formed on each well of a gelatin-coated 6 well plate, and an ES cell is added by dropping thereto to carry out culture thereon. In such a method, contamination of the feeder cell occurs in some cases when the ES cell culture is recovered from a carrier for culture after the culture by pipetting or the like means.

On the other hand, mixing of a cultured cell with a feeder cell can be prevented by mounting the carrier for culture of the present invention described above on the feeder cell layer and culturing the undifferentiated cell on the carrier for culture.

Additionally, according to the method of the present invention for culturing a cell, ES cell can be easily cultured without using a feeder cell.

Also, subculture can be carried out by separating the cell mass obtained by the initial stage (primary) culture into a single cell or a small cell population, and repeating secondary culture, tertiary culture and so forth using the obtained undifferentiated cell in the same manner as in the culture method described above.

The cells to be cultured in the present invention are undifferentiated cells typified by ES cells.

The undifferentiated cell is a cell under a state of undifferentiation, which has the ability to proliferate into a cell identical to itself and the ability to differentiate into a certain tissue cell by the provision of a differentiation induction factor and cannot return to its undifferentiated state when once differentiated into other tissue cell. Examples thereof include, embryonic stem cell (ES cell), mesenchymal stem cell, hematopoietic stem cell, neural stem cell, liver stem cell, pancreas stem cell, skin stem cell and the like.

Among the undifferentiated cells, it is preferable to use ES cell or mesenchymal stem cell in the present invention.

According to the present invention, it is possible to culture the undifferentiated cell by directly inoculating on the carrier for culture consisting of ceramics without mediating supporting cells typified by a feeder cell, and such an embodiment is preferable.

By the direct inoculation on the ceramic carrier for culture, contamination of the undifferentiated cell to be cultured with other cell-derived risk factor can be prevented.

Additionally, the medium to be used in the culturing method concerned in the present invention is not particularly limited and can be appropriately selected according to the cell to be cultured. For example, MEM, α-MEM, DMEM, Eagle's medium and the like can be suitably used.

In general, FBS (fetal bovine serum), KSR (KnockOut™ Serum Replacement), LIF (leukemia inhibitory factor), bFGF (basic fibroblast growth factor) and the like are added to the media, and it is preferable to further add nonessential amino acids, pyruvic acid, mercaptoethanol and the like for proliferation support.

In carrying out the subculture, an ES cell is inoculated on the carrier for culture, and when inside of the concavity is completely filled up with the proliferated cell, the ES cell is again inoculated on another carrier for culture.

In carrying out the re-inoculation, it is necessary to exfoliate the cell mass from the carrier for culture and separate it into a single cell or small cell population. It can be carried out by enzyme treatment such as trypsin for a short time or by pipetting for several times.

It is preferable that the undifferentiated cell obtained by culturing it using the method keeps expression of undifferentiation markers typified by an alkaline phosphatase.

When these are confirmed, it can be understood that the ES cell is under undifferentiated state. Namely, the undifferentiated state can be confirmed by staining an antigen which is expressed under undifferentiated state, while it is not expressed under differentiated state and thereby confirming that an undifferentiation marker such as the alkaline phosphatase or the like is expressed.

According to the method in the present invention for culturing a cell, the subculture can be carried out under the state of maintaining the aforementioned characteristics.

Additionally, when the cell mass obtained in the above is exfoliated from the carrier for culture in the form of the cell mass, suspension culture can be carried out using the cell mass of undifferentiated cell.

Thus, the cell mass of undifferentiated cell obtained by the present invention can be suitably applied not only to its subculture but also to its suspension culture. An embryoid body (EB) can be easily obtained from the ES cell by the suspension culture.

In this connection, as described in the above, the ES cell of primates such as human and monkey cannot survive when its cell mass is completely separated by the trypsin treatment. On the other hand, when the carrier for culture of the present invention is used, the cultured cell is so easily separable that it can be exfoliated from the carrier for culture as it is in the state of cell mass by pipetting alone without carrying out enzyme treatment with such as trypsin. Additionally, by carrying out suspension culture of this cell mass as it is, embryoid body (EB) having uniform size can be easily formed.

As described above, according to the carrier for cell culture of the present invention, since a certain concavity on its substrate surface forms a physical barrier, culture of an undifferentiated cell can be carried out with keeping its undifferentiated state in the concavity. Additionally, handling of the cultured cell mass also becomes easy.

Also, since the concavity surface of the carrier for culture is constituted by a porous body, the cultured cell mass can be easily exfoliated from the carrier for culture and a cultured cell having a uniform size can be conveniently obtained.

Additionally, according to the method for cell culture of the present invention which uses the carrier for culture described above, an undifferentiated cell can be sub-cultured efficiently in a large amount without using a feeder cell with its undifferentiated state.

Accordingly, the present invention can contribute to the development of techniques for culturing undifferentiated cells such as ES cell and multipotential adult stem cell having pluripotency and further to the application of living body tissues to regeneration treatment.

EXAMPLES

Although the present invention described further illustratively based on Examples, the present invention is not limited by the following Examples.

Example 1

A carrier for culture consisting of an alumina ceramics porous body on which hemisphere concavities each having a diameter of 250 µm were arranged in the form of a matrix was put into each well of a 24 well plate under aseptic condition. An electron microphotograph (20,000 magnifications) of the aluminum ceramics porous body is shown in FIG. 1.

On the carrier for culture, 1 mL of $3.0 \times 10^4$ cells/mL mouse ES cell suspension was inoculated and incubated at 37° C. for 3 days in a 5% $CO_2$ incubator using DMEM containing KSR, LIF, pyruvic acid, nonessential amino acids and mercaptoethanol.

Additionally, undifferentiated state of the ES cell colonies after the culturing was detected by carrying out an alkaline phosphatase staining using an alkaline phosphatase tissue staining kit (86-R; manufactured by SIGMA) based on the following operation.

After suction removal of the medium in the 24 well plate and subsequent washing with PBS buffer, fixation treatment was carried out using an aldehyde solution. Further, this fixation-treated carrier and the staining liquid were put into a 15 mL tube and allowed to stand still at room temperature for 30 to 60 minutes to effect the staining.

Figure 2:
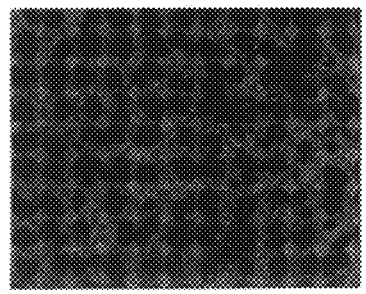

A microphotograph (50 magnifications) of the cells after staining is shown in FIG. 2.

Based on the stained conditions shown in the microphotograph of FIG. 2, it was confirmed that the cultured mouse ES cells formed almost uniform colonies. The undifferentiation was confirmed by the alkaline phosphatase activity.

Figure 3:
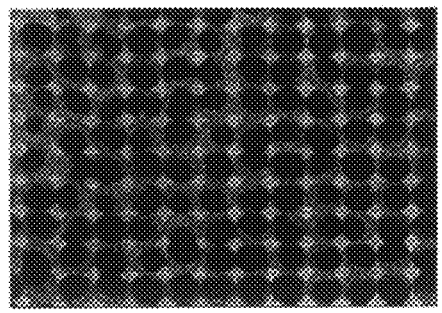

Additionally, FIG. 3 shows a microphotograph (50 magnifications) of the carrier for culture after the staining of the cultured cells with alkaline phosphatase described above and subsequent recovery by pipetting without carrying out the trypsin treatment.

It was able to exfoliate the cultured mouse ES cell colonies by pipetting without carrying out the trypsin treatment and to recover them almost completely without damaging them, which can be seen from the microphotograph of FIG. 3.

Comparative Example 1

Figure 4:
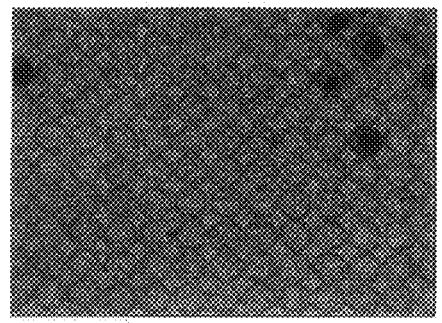

In the same manner as in Example 1, culture of mouse ES cell was carried out by using, an alumina ceramics compact body on which hemisphere concavities each having a diameter of 250 µm were arranged in the form of a matrix as the carrier for culture. An electron microphotograph (20,000 magnifications) of the aluminum ceramics compact body is shown in FIG. 4.

Figure 5:
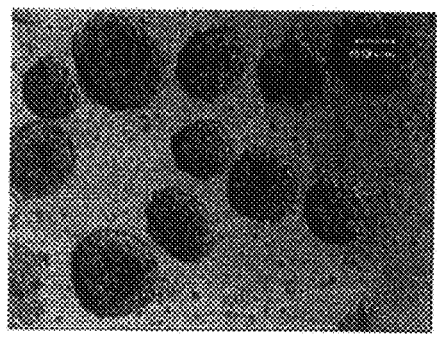

Also, a microphotograph (50 magnifications) of the cultured cells after alkaline phosphatase staining is shown in FIG. 5.

Based on the stained conditions shown in the microphotograph of FIG. 5, it was confirmed that the cultured mouse ES cells formed colonies although the colonies were not uniform. The undifferentiation was confirmed by the alkaline phosphatase activity.

Figure 6:
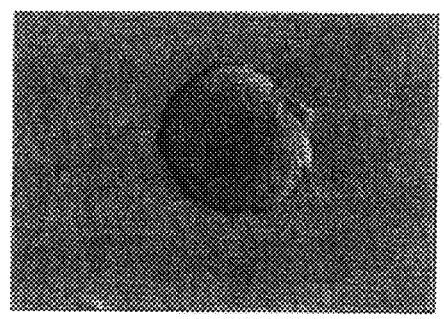

Additionally, FIG. 6 shows a microphotograph (50 magnifications) of the carrier for culture after the alkaline phosphatase staining of the cultured cells with alkaline phosphatase and subsequent recovery by pipetting without carrying out the trypsin treatment.

It was not able to exfoliate the cultured mouse ES cell colonies from the carrier for culture by pipetting and they were partially adhered to and remained on the carrier for culture which can be seen from the microphotograph of FIG. 6.

Comparative Example 2

Figure 7:
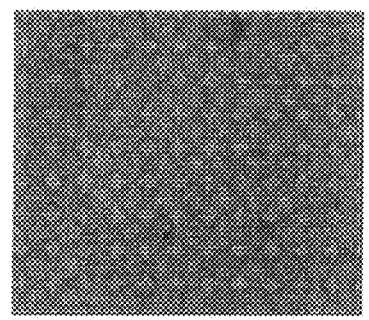

In the same manner as in Example 1, culture of mouse ES cell was carried out by using a smooth zirconia ceramics having no concavities as the carrier for culture. An electron microphotograph (100 magnifications) of the carrier for culture is shown in FIG. 7.

Figure 8:
FIG. 8 is a microphotograph (50 magnifications) of cultured cells on the carrier for culture in Comparative Example 2 after alkaline phosphatase staining.

Also, a microphotograph (50 magnifications) of the cultured cells after alkaline phosphatase staining is shown in FIG. 8.

Based on the stained conditions shown in the microphotograph of FIG. 8, it was confirmed that colonies of the cultured mouse ES cell showed distorted shapes and became huge. Also, degree of the alkaline phosphatase staining was poor, which shows a tendency of reduction of the undifferentiation.

Example 2

Figure 9:
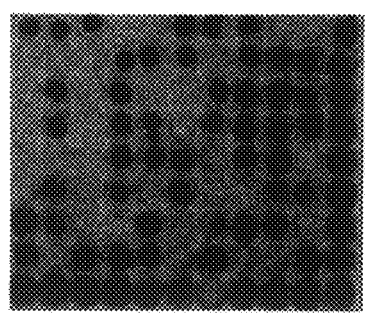
FIG. 9 is an electron microphotograph (100 magnifications) of the carrier for culture in Example 1.

A feeder cell layer was formed on each well of a gelatin-coated 24 well plate by a $2.5 \times 10^5$ cells/mL cell suspension of mitomycin-treated MEF (mouse embryonic fibroblast). A carrier for culture consisting of a zirconia ceramics porous body on which hemisphere concavities each having a diameter of 800 µm were arranged in the form of a matrix was soaked therein. An electron microphotograph (200 magnifications) of the carrier for culture is shown in FIG. 9.

After treating previously sub-cultured human ES cell with a collagenase-trypsin solution and carrying out pipetting, 400 cells/mL cell suspension containing a cell mass of about 200 µm in diameter was inoculated on the carrier for culture and incubated at 37° C. for 5 days in a 5% $CO_2$ incubator using DMEM containing bFGF (basic fibroblast growth factor), KSR, pyruvic acid and nonessential amino acids.

Additionally, undifferentiated state of the human ES cell colonies after the culturing was detected by carrying out an alkaline phosphatase staining using an alkaline phosphatase tissue staining kit (86-R; manufactured by SIGMA) based on the following operation.

After suction removal of the medium in the 24 well plate and subsequent washing with PBS buffer, fixation treatment was carried out using aldehyde solution. Further, the fixation-treated carrier and the staining liquid were put into a 15 mL capacity tube and allowed to stand still at room temperature for 30 to 60 minutes to effect the staining.

Figure 10:
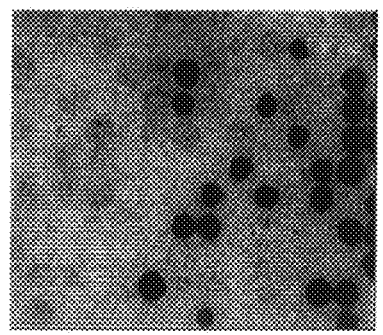
FIG. 10 is a microphotograph (200 magnifications) of cultured cells on the carrier for culture in Example 2 after alkaline phosphatase staining.

A microphotograph (200 magnifications) of the cells after staining is shown in FIG. 10.

Based on the stained conditions shown in the microphotograph of FIG. 10, it was confirmed that the cultured mouse ES cells formed cell colonies in the concavities of the zirconia ceramics. The state of undifferentiation of the ES cell colonies was confirmed by the alkaline phosphatase activity.

Example 3

The mouse ES cell was cultured for 3 days in the same manner as in Example 1.

After the culture, DMEM was removed by suction by an aspirator, and the mouse ES cell colonies cultured in the concavities of the carrier for culture were exfoliated by pipetting using IMDM containing FBS, pyruvic acid, nonessential amino acids and mercaptoethanol.

Figure 11:
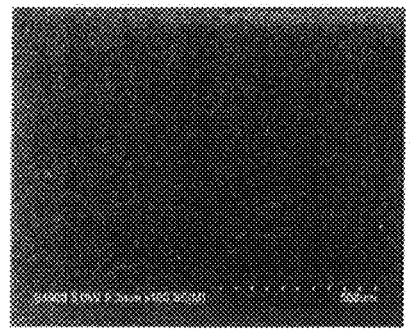
FIG. 11 is a microphotograph (50 magnifications) of cultured cells on the carrier for culture in Example 3 after alkaline phosphatase staining.
Figure 12:
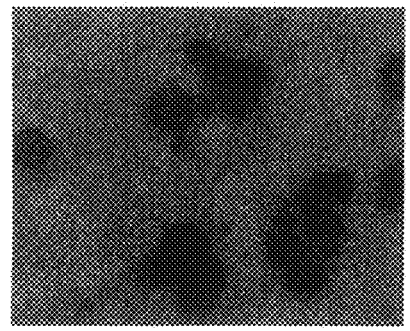
FIG. 12 is a microphotograph (50 magnifications) of the carrier for culture in Example 3 after pipetting.

A microphotograph (50 magnifications) after the alkaline phosphatase staining of cultured cells is shown in FIG. 11. Also, a microphotograph (50 magnifications) of the carrier for culture after recovery of the alkaline phosphatase-stained cultured cells by pipetting is shown in FIG. 12.

Based on the stained conditions shown in the microphotograph of FIG. 11, it was confirmed that the cultured mouse ES cells formed almost uniform colonies. The undifferentiation was confirmed by the alkaline phosphatase activity. Additionally, it was able to exfoliate the cultured mouse ES cell colonies easily from the carrier for culture by pipetting without carrying out the trypsin treatment and to recover them almost completely without damaging them, which can be seen from the microphotograph of FIG. 12.

Figure 13:
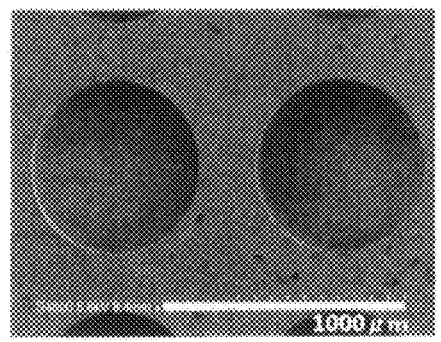
FIG. 13 is a microphotograph (100 magnifications) of cultured mouse ES cell colonies on the non-contacting plate in Example 3.

Additionally, FIG. 13 shows a microphotograph (100 magnifications) of the aforementioned mouse ES cell colonies exfoliated from the concavities, just after their transfer on a non-contacting plate.

Based on the microphotograph of FIG. 13, it was confirmed that spherical mouse ES cell colonies having a diameter of from 150 to 200 µm were suspended.

Next, mouse EBs were formed by transferring the mouse ES cell colonies exfoliated from the concavities to a 6 cm dish coated with a cell-non-adhesion molecule and then carrying out suspension culture at 37° C. for 5 days in a 5% $CO_2$ incubator.

Figure 14:
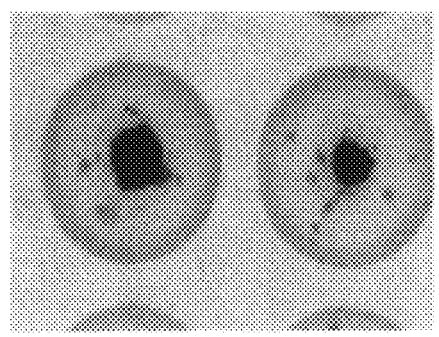
FIG. 14 is a microphotograph (100 magnifications) of mouse EB obtained by the suspension culture in Example 3.

A microphotograph (100 magnifications) of the mouse EBs after culturing is shown in FIG. 14.

It was confirmed from the microphotograph shown in FIG. 14 that spherical mouse EBs having a diameter of 300 µm were suspended.

Additionally, when expression of markers specific to undifferentiation, ectoderm, mesoderm and endoderm was verified by recovering mRNA from each mouse EB and carrying out its conversion into DNA by RT-PCR and amplification of the DNA fragment by PCR, it was confirmed that EB was differentiated into ectoderm, mesoderm and endoderm.

Example 4

A carrier for culture consisting of zirconia ceramics was soaked in each well of a 24 well plate, and mouse ES cell which had been cultured in advance was inoculated at a density of $3.0 \times 10^4$ cells per one concavity and cultured at 37° C. for 3 days in a 5% $CO_2$ incubator using DMEM medium containing KSR, pyruvic acid, nonessential amino acids and LIF.

Figure 15:
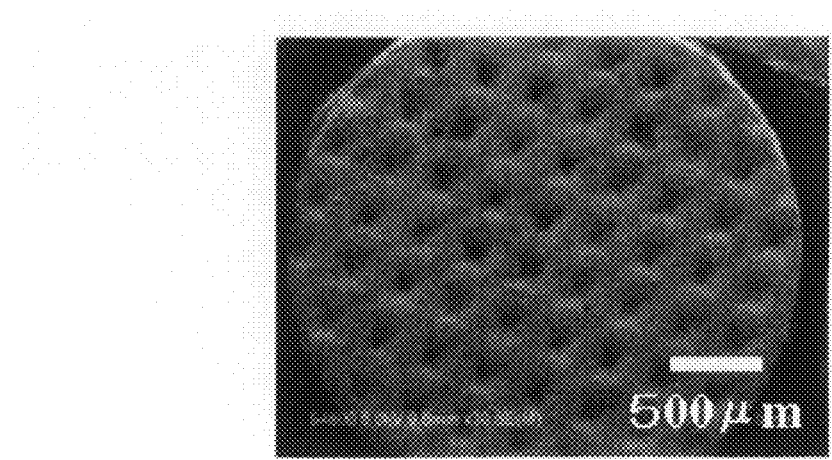
FIG. 15 is an electron microphotograph (30 magnifications) of the zirconia ceramics carrier for culture in Example 4.
Figure 16:
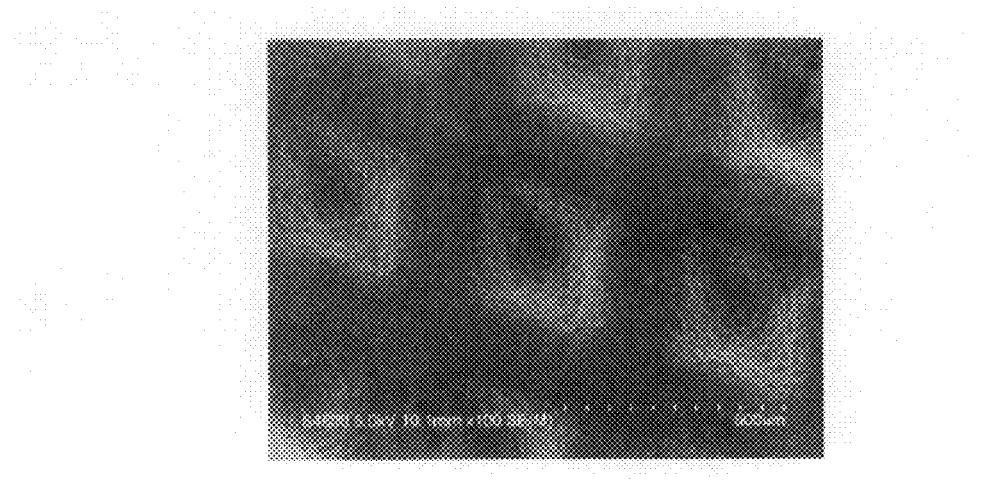
FIG. 16 is an electron microphotograph (100 magnifications) of the zirconia ceramics carrier for culture in Example 4.

A zirconia ceramic having a surface shape in which an inverse quadrangular concavity having a diameter of about 300 µm was regularly arranged was used in the culture described above as the carrier for culture. Electron microphotographs (30 and 100 magnifications) of the carrier for culture are respectively shown in FIGS. 15 and 16.

Figure 17:
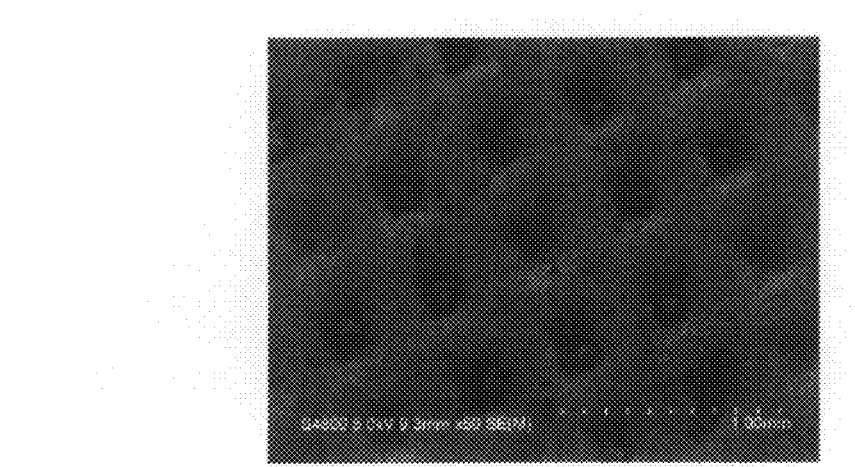
FIG. 17 is an electron microphotograph (50 magnifications) of cells cultured on the zirconia ceramics carrier for culture in Example 4.
Figure 18:
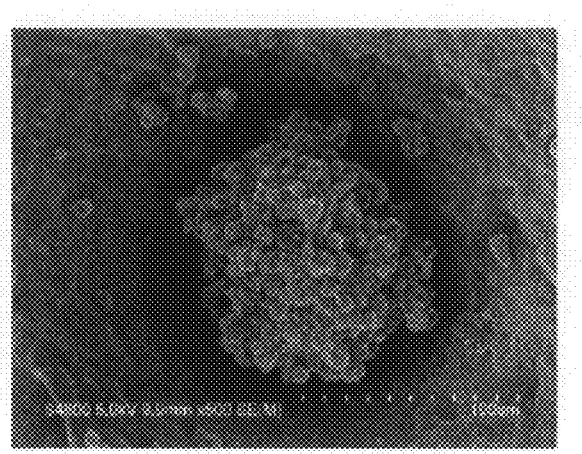
FIG. 18 is an electron microphotograph (500 magnifications) of cells cultured on the zirconia ceramics carrier for culture in Example 4.

Also, electron microphotographs (50 and 500 magnifications) of the cells after culture are shown in FIGS. 17 and 18.

It was confirmed that ES cell colonies were formed in the concavities on the surface of the zirconia ceramic carrier for culture, which can be seen from the electron microphotographs of FIGS. 17 and 18.

Additionally, undifferentiated state of the ES cell colonies after the culture was detected by carrying out an alkaline phosphatase staining using an alkaline phosphatase tissue staining kit (86-R; manufactured by SIGMA) based on the following operation.

After suction removal of the medium in the 24 well plate and subsequent washing with PBS buffer, fixation treatment was carried out using aldehyde solution. Further, the fixation-treated carrier and the staining liquid were put into a 15 mL tube and allowed to stand still at room temperature for 30 to 60 minutes to effect the staining.

Figure 19:
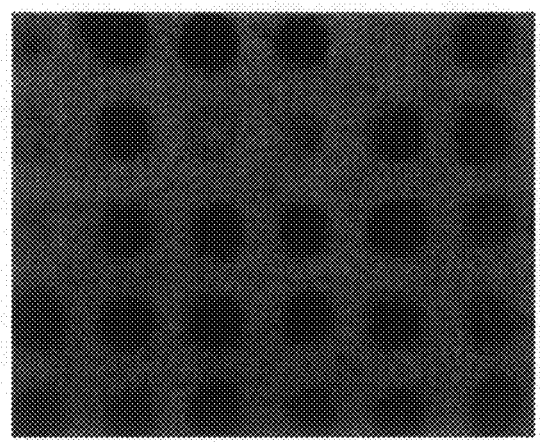
FIG. 19 is a microphotograph (50 magnifications) of cells which were cultured on the zirconia ceramics carrier for culture and stained with alkaline phosphatase in Example 4.

A microphotograph (50 magnifications) of the cells after staining is shown in FIG. 19.

Based on the stained conditions shown in the microphotograph of FIG. 19, it was confirmed that the cultured mouse ES cells formed almost uniform colonies. The state of undifferentiation was confirmed by the alkaline phosphatase activity.

Example 5

Figure 20:
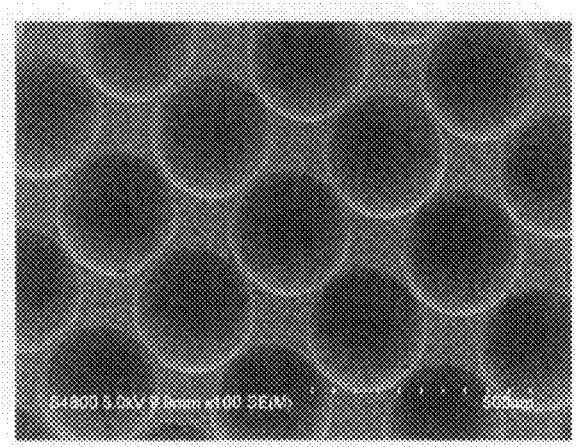
FIG. 20 is an electron microphotograph (100 magnifications) of the zirconia ceramics carrier for culture in Example 5.

In the same manner as in Example 1, culture of the mouse ES cell was carried out by using a zirconia ceramic having a surface shape in which a hemispheric concavity having a diameter of about 250 µm was regularly arranged. An electron microphotograph (100 magnifications) of the carrier for culture is shown in FIG. 20.

Figure 21:
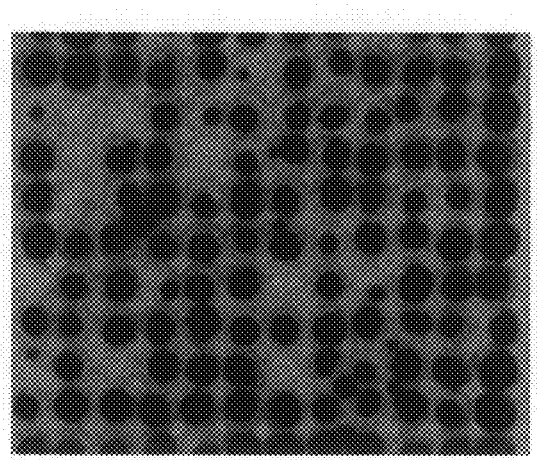
FIG. 21 is a microphotograph (50 magnifications) of cells which were cultured on the zirconia ceramics carrier for culture and stained with alkaline phosphatase in Example 5.

Also, a microphotograph after alkaline phosphatase staining after the culture is shown in FIG. 21.

Based on the stained conditions shown in the microphotograph of FIG. 21, it was confirmed that the cultured mouse ES cells formed almost uniform colonies. The state of undifferentiation was confirmed by the alkaline phosphatase activity.

Example 6

Figure 22:
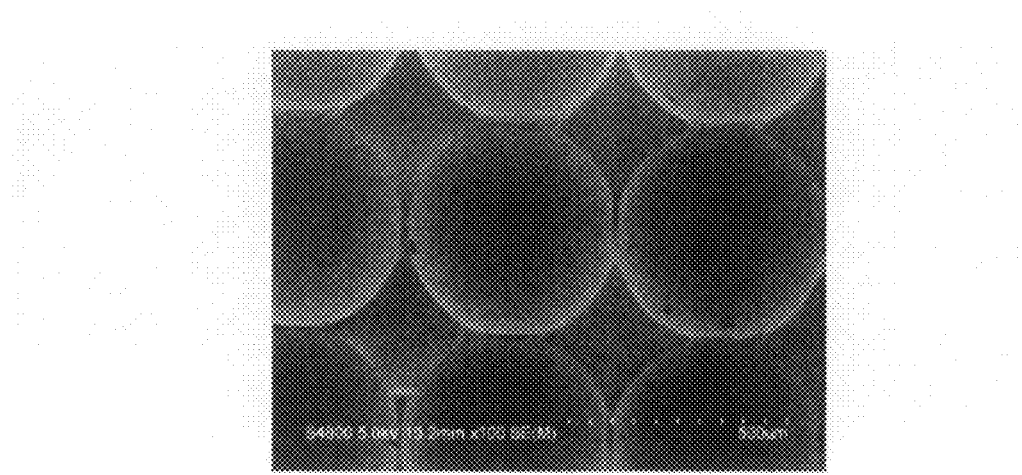
FIG. 22 is an electron microphotograph (100 magnifications) of the zirconia ceramics carrier for culture in Example 6.

In the same manner as in Example 4, culture of the mouse ES cell was carried out by using a zirconia ceramic having a surface shape in which a hemispheric concavity having a diameter of about 450 µm was regularly arranged. An electron microphotograph (100 magnifications) of the carrier for culture is shown in FIG. 22.

Figure 23:
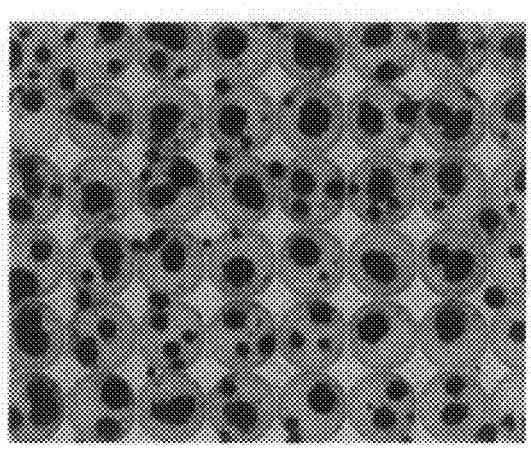
FIG. 23 is a microphotograph (50 magnifications) of cells which were cultured on the zirconia ceramics carrier for culture and stained with alkaline phosphatase in Example 6.

Also, a microphotograph after alkaline phosphatase staining after the culture is shown in FIG. 23.

Based on the stained conditions shown in the microphotograph of FIG. 23, although the state of undifferentiation of the cultured mouse ES cells was confirmed by the alkaline phosphatase activity, the cell colonies in the concavities of the carrier for culture did not become spherical single colonies and two or more colonies having distorted shapes were present therein.

Comparative Example 3

Figure 24:
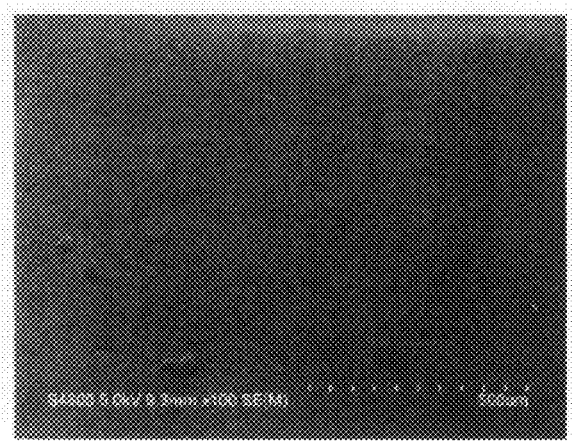
FIG. 24 is an electron microphotograph (100 magnifications) of the carrier for culture in Comparative Example 3.

In the same manner as in Example 4, culture of the mouse ES cell was carried out by using a smooth zirconia ceramic having no concavities as the carrier for culture. An electron microphotograph (100 magnifications) of the carrier for culture is shown in FIG. 24.

Figure 25:
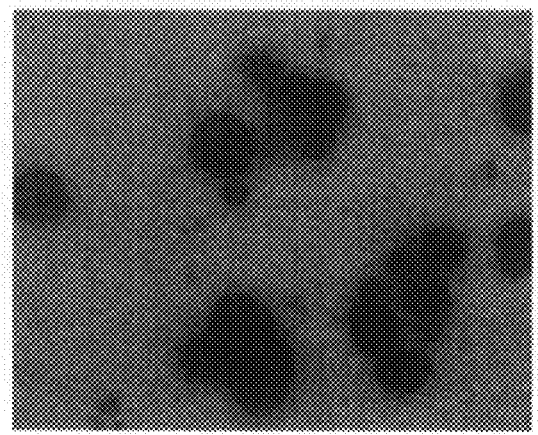
FIG. 25 is a microphotograph (50 magnifications) of cells which were cultured on the zirconia ceramics carrier for culture and stained with alkaline phosphatase in Comparative Example 3.

Also, a microphotograph after alkaline phosphatase staining after the culture is shown in FIG. 25.

Based on the stained conditions shown in the microphotograph of FIG. 25, it was confirmed that colonies of the cultured mouse ES cell showed distorted shapes and became huge. Also, degree of the alkaline phosphatase staining was poor, which shows a tendency of reduction of the undifferentiation.

What is claimed is:

1. A carrier for cell culture, comprising concavities arranged in line direction and column direction on a surface of the carrier, wherein the whole carrier, including the surface, consists of a porous body and wherein a cultured cell is capable of adhering to the inside of each of the concavities, and wherein the porous body has a pore size of from 10 nm to 2,000 nm, and wherein the porous body consists of at least one material selected from the group consisting of zirconia, yttria, titania, alumina, hydroxyapatite, and β-calcium tertiary phosphate, and wherein the concavities each have a diameter from 10 μm to 1,000 μm and a depth of from 30 μm to 1,000 μm.

2. The carrier according to claim 1, wherein the concavities have a bottom of a hemispheric shape.

3. The carrier according to claim 1, wherein the concavities each have a diameter of from 100 μm to 400 μm and a depth of from 50 μm to 400 μm, wherein the concavities are each capable of culturing a mouse ES cell.

4. The carrier according to claim 1, wherein the concavities each have a diameter of from 250 μm to 1,000 μm and a depth of from 125 μm to 1,000 μm, wherein the concavities are each capable of culturing a human ES cell.

5. The carrier according to claim 1, wherein the porous body is selected from the group consisting of zirconia and alumina.

6. A method for culturing a cell, which comprises using the carrier of claim 1, inoculating an undifferentiated cell on at least one concavity of the carrier for cell culture and carrying out a culture.

7. A method for culturing a cell, which comprises carrying out a subculture by repeating the method for culturing described in claim 6, by separating a cell mass obtained by culture into a single cell or a small cell population, and using the cell obtained by exfoliation from the carrier for culture.

8. The method for culturing a cell according to claim 7, wherein separating the cell mass is carried out by enzyme treatment and pipetting.

9. A method for culturing a cell, which comprises carrying out suspension culture by exfoliating the cell mass obtained in claim 7 from the carrier for culture in the state of cell mass, and using the cell mass.

10. The method for culturing a cell according to claim 9, wherein exfoliating the cell mass from the carrier for cell culture is carried out by pipetting alone.

* * * * *